United States Patent [19]

Sunley

[11] Patent Number: 5,834,622
[45] Date of Patent: Nov. 10, 1998

[54] PROCESS FOR THE CARBONYLATION OF A CARBONYLATABLE REACTANT

[75] Inventor: John Glenn Sunley, Cottingham, England

[73] Assignee: BP Chemicals Limited, London, England

[21] Appl. No.: 676,056

[22] Filed: Jul. 5, 1996

[51] Int. Cl.⁶ ............................ C07C 67/36; C07C 51/12; C07C 51/14
[52] U.S. Cl. .......................... 560/232; 560/233; 562/517; 562/519; 562/520; 562/522
[58] Field of Search ..................................... 560/232, 233; 562/517, 519, 520, 522

[56] References Cited

FOREIGN PATENT DOCUMENTS 0 643 034   3/1995   European Pat. Off. .

Primary Examiner—Gary Geist
Assistant Examiner—Rosalynd Keys
Attorney, Agent, or Firm—Fay, Sharpe, Beall, Fagan Minnich & McKee

[57] ABSTRACT

A process for the carbonylation of a carbonylatable reactant having a carbonylatable moiety having at least two carbon atoms and/or a reactive derivative thereof which process comprises contacting said carbonylatable reactant and/or a reactive derivative thereof with carbon monoxide in a liquid reaction composition in a carbonylation reactor characterized in that the liquid reaction composition comprises: (a) an iridium catalyst, (b) a halide, (c) at least a finite concentration of water, (d) a carbonylatable reactant having a carbonylatable moiety having at least two carbon atoms and/or a reactive derivative thereof and (e) as promoter, at least one of ruthenium and osmium.

17 Claims, No Drawings

PROCESS FOR THE CARBONYLATION OF A CARBONYLATABLE REACTANT

The present invention relates to a carbonylation process and, in particular, to a carbonylation process using an iridium catalyst.

European patent application number 94306506.0 describes to a process for the production of acetic acid by carbonylation of methanol and/or a reactive derivative thereof in the presence of an iridium catalyst and as promoter, at least one of ruthenium and osmium.

The technical problem to be solved is to provide a process for the carbonylation of a carbonylatable reactant having a carbonylatable moiety having at least two carbon atoms or a reactive derivative thereof in the presence of an iridium catalyst.

Thus, according to the present invention there is provided a process for the carbonylation of a carbonylatable reactant having a carbonylatable moiety having at least two carbon atoms and/or a reactive derivative thereof which process comprises contacting said carbonylatable reactant and/or a reactive derivative thereof with carbon monoxide in a liquid reaction composition in a carbonylation reactor characterised in that the liquid reaction composition comprises: (a) an iridium catalyst, (h) a halide, (c) at least a finite concentration of water, (d) a carbonylatable reactant having a carbonylatable moiety having at least two carbon atoms and/or a reactive derivative thereof and (e) as promoter, at least one of ruthenium and osmium.

Suitable carbonylatable reactants having a carbonylatable moiety having at least two carbon atoms include alcohols, esters, ethers, hydrocarbyl halides and olefins and suitable reactive derivatives thereof include esters, ethers and hydrocarbyl halides.

Suitable alcohol reactants include monofunctional aliphatic alcohols, aliphatic diols and aliphatic polyols. Preferably, the alcohol is selected from the group consisting of monofunctional alkyl alcohols, alkyl diols and alkyl polyols. Preferably, the monofunctional alkyl alcohol is a $C_2$ to $C_6$ monofunctional alkyl alcohol, more preferably a $C_2$ to $C_4$ monofunctional alkyl alcohol, most preferably ethanol. Preferably, the alkyl diol is a $C_2$ to $C_6$ alkyl diol, more preferably a $C_2$ to $C_4$ alkyl diol, most preferably 1,4-butanediol. Preferably, the alkyl polyol is a $C_2$ to $C_6$ alkyl polyol, most preferably a $C_2$ to $C_4$ alkyl polyol. A mixture of one or more alcohols reactants and/or reactive derivatives thereof may be used as reactants in the process of the present invention. Preferably, ethanol and or ethyl propionate are used as reactants.

Suitable ester reactants include esters of an alcohol and a carboxylic acid. Preferably, the ester is an ester of a carboxylic acid and a $C_2$ to $C_6$ monofunctional alkyl alcohol, more preferably an ester of a carboxylic acid and a $C_2$ to $C_4$ monofunctional alkyl alcohol, most preferably an ester of a carboxylic acid and ethanol or propanol. Preferably, the ester is an ester of an alcohol and the carboxylic acid product. A particularly preferred ester is ethyl propionate. Other suitable esters include cyclic esters having from 3 to 6 carbon atoms. Preferably, the cyclic ester is a lactone, most preferably valerolactone. A mixture of esters and/or reactive derivatives thereof may be used as reactants in the process of the present invention.

Suitable ether reactants include hydrocarbyl ethers. Preferably, the ether reactant is a dialkyl ether having $C_2$ to $C_6$ alkyl moieties, more preferably a dialkyl ether having $C_2$ to $C_4$ alkyl moieties, most preferably diethyl ether or dipropyl ether. A mixture of ethers and/or reactive derivatives thereof may he used as reactants in the process of the present invention.

Suitable hydrocarbyl halide reactants include alkyl halides. Preferably, the alkyl halide is an iodide. Preferably, the hydrocarbyl halide is an $C_2$ to $C_6$ alkyl halide, more preferably a $C_2$ to $C_4$ alkyl halide, most preferably ethyl iodide or propyl iodide. A mixture of hydrocarbyl halides and/or reactive derivatives thereof may be used as reactants in the process of the present invention.

Suitable olefins include monofunctional olefins and dienes. Preferably, the monofunctional olefin is a $C_2$ to $C_6$ monofunctional olefin, more preferably a $C_2$ to $C_4$ monofunctional olefin, most preferably ethylene. Preferably, the diene is a $C_4$ to $C_6$ diene, more preferably butadiene. A mixture of olefins may be used as reactants in the process of the present invention. Where the carbonylatable reactant is an olefin, water is consumed as a reactant in addition to carbon monoxide.

A mixture of alcohol, ester, ether, hydrocarbyl halide aid olefin carbonylatable reactants independently having a carbonylatable moiety having at least two carbon atoms and/or reactive derivatives thereof may be used in the process of the present invention.

It is also envisaged that carbonylatable reactant having a carbonylatable moiety having at least two carbon atoms may be co-fed to the reactor with methanol and/or a reactive derivative thereof such as methyl acetate, in which case acetic acid and/or methyl acetate will be a co-product of the carbonylation reaction. A particularly preferred embodiment is to co-feed methanol and/or (methyl acetate and water) with (ethylene and water) and/or ethanol and/or (ethyl acetate and water) to co-produce acetic acid and propionic acid.

At least some of the one or more carbonylatable reactants having a carbonylatable moiety having at least two carbon atoms and/or reactive derivatives thereof will be converted to, and hence present as, esters in the liquid reaction composition by reaction with carboxylic acid product or solvent.

The concentration in the liquid reaction composition, of the alcohol, ester, ether or hydrocarbyl halide reactant and/or a reactive derivative thereof is suitably in the range 1 to 70% by weight, preferably 2 to 50% by weight most preferably 3 to 35% by weight.

The product of the carbonylation reaction is the corresponding carboxylic acid having at least one more carbon atom than the carbonylatable reactant and/or is the ester formed by reaction of the carboxylic acid with alcohol reactant (where the carbonylatable reactant includes an alcohol) or with a derivative of the carbonylatable reactant. Examples of carboxylic acids that may be produced using the process of the present invention include propionic acid and adipic acid.

Preferably, the concentration of water in the liquid reaction composition is in the range 0.1 to 15% by weight, more preferably 1 to 15% by weight, most preferably 1 to 10% by weight.

The iridium catalyst in the liquid carbonylation reaction composition may comprise any iridium containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2)Br]_2$, $[Ir(CO)_2I_2]^-$, $[Ir(CO)_2Br_2]^-$, $[Ir(CO)_4I_2]^-$, $[Ir(CH_3)I_3(CO)_2]^-$, $Ir_4(CO)_{12}$ $IrCl_3$, $4H_2O$, $IrBr_3$, $4H_2O$, $Ir_3(CO)_{12}$, iridium metal, $Ir_2O_3$, $IrO_2$, $Ir(acac)(CO)_2$, $Ir(acac)_3$, iridium acetate $[Ir_3O(OAc)_6$ ($H_2O)_3$][OAc], and hexachloroiridic acid [$H_2IrCl_6$] preferably, chloride-free complexes of iridium such as acetates, oxalates and acetoacetates.

Preferably, the iridium catalyst concentration in the liquid reaction composition is in the range 100 to 6000 ppm by weight of iridium.

The ruthenium and/or osmium promoter may comprise any ruthenium and/or osmium containing compound which is soluble in the liquid reaction composition. The promoter may be added to the liquid reaction composition for the carbonylation reaction in any suitable form which dissolves in the liquid reaction composition or is convertible to soluble form.

Examples of suitable ruthenium-containing compounds which may be used include ruthenium (III) chloride, ruthenium (III) chloride trihydrate, ruthenium (IV) chloride, ruthenium (III) bromide, ruthenium metal, ruthenium oxides, ruthenium (III) formate, [$Ru(CO)_3I_3$]$^-$H', tetra (aceto)chlororuthenium(II,III), ruthenium (III) acetate, ruthenium (III) propionate, ruthenium (III) butyrate, ruthenium pentacarbonyl, triruthemiumdodecacarbonyl and mixed ruthenium halocarbonyls such as dichlorotricarbonylruthenium (II) dimer, [$Ru(CO)_4I_2$], [{$Ru(CO)_3I_2$}$_2$], dibromotricarbonylruthenium (II) dimer, and other organoruthenium complexes such as tetrachlorobis(4-cymene) diruthenium(II), tetrachlorobis(benzene)diruthenium(II), dichloro(cycloocta-1,5-diene)ruthenium (II) polymer and tris(acetylacetonate)ruthenium (III).

Examples of suitable osmium containing compounds which may be used include osmium (III) chloride hydrate and anhydrous, osmium metal, osmium tetraoxide, triosmiumdodecacarbonyl, and mixed osmium halocarbonyls such as tricarbonyldichloroosmium (II) dimer, [$Os(CO)_4I_2$] and other organoosmium complexes.

The molar ratio of each promoter to iridium catalyst is suitably in the range 0.1:1 to 15.1, preferably 0.5:1 to 10:1.

Suitably, the halide is hydrogen halide and/or a $C_1$ to $C_6$ alkyl halide, preferably a $C_1$ to $C_4$ alkyl halide. Preferably, the halide is an iodide. Preferably, the alkyl halide has an alkyl moiety corresponding to that of the reactant. Where the carboxylic acid product is propionic acid the alkyl iodide is preferably ethyl iodide.

Preferably, the concentration of halide in the liquid reaction composition is in the range 1 to 20% by weight, preferably 2 to 15% by weight.

The partial pressure of carbon monoxide in the reaction is suitably in the range 1 to 70 bar, preferably 1 to 35 bar and most preferably 1 to 15 bar. The promoters of the present invention are particularly beneficial at relatively low partial pressures of carbon monoxide in the reactor (less than 15 bar) when the rate may otherwise be dependent upon the carbon monoxide partial pressure.

The total pressure of the carbonylation reaction is suitably in the range 10 to 200 barg, preferably 10 to 100 barg, most preferably 15 to 50 barg. The temperature of the carbonylation reaction is suitably in the range 100° to 300° C., preferably in the range 150° to 220° C.

A carboxylic acid may be used as solvent for the reaction and preferably the carboxylic acid product is used as solvent for the reaction.

The carboxylic acid and/or ester product may be removed from the reactor by withdrawing liquid reaction composition and separating the carboxylic acid and/or ester product by one or more flash and/or fractional distillation stages from the other components of the liquid reaction composition such as iridium catalyst, ruthenium and/or osmium promoter, halide, water and unconsumed reactants which may be recycled to the reactor to maintain their concentrations in the liquid reaction composition. The carboxylic acid and/or ester product may also be removed as a vapour from the reactor.

The process of the present invention may be performed as a batch or continuous process, preferably as a continuous process.

The invention will now be illustrated by way of example only by reference to the following examples.

EXAMPLE 1 AND COMPARATIVE EXPERIMENT A

These experiments were performed using a 100 ml Hastelloy B2 (Trade Mark) autoclave equipped with a Dispersimax (Trade Mark) stirrer and liquid catalyst injection facility. A gas supply to the autoclave was provided from a gas ballast vessel, feed gas being provided to maintain the autoclave at a constant pressure. The rate of gas uptake at a certain point in a reaction run was used to calculate the carbonylation rate, as number of moles of reactant consumed per liter of cold degassed reactor composition per hour (mol/l/hr), at a particular reactor composition (reactor composition based on a cold degassed volume).

The ethyl propionate concentration was calculated during the course of the reaction from the starting composition, assuming that one mole of ethyl propionate is consumed for every mole of carbon monoxide that is consumed. No allowance was made for organic components in the autoclave headspace.

For each batch carbonylation experiment the iridium catalyst ($II_2IrCl_6$), dissolved in a portion of the propionic acid/water liquid reactor charge, was charged to the liquid injection facility. If a catalyst promoter was used this was dissolve in the remaining reactor charge. The remaining charge and optional catalyst promoter were then charged to the autoclave. The autoclave was sealed, flushed with carbon monoxide (2×6 bars), pressurised with carbon monoxide to 6 barg and heated with stirring (1100 rpm) to reaction temperature. The total pressure in the autoclave was then raised to approximately 3 barg below the desired operating pressure by feeding carbon monoxide from the ballast vessel. Once stable at temperature the catalyst was injected using an over pressure of carbon monoxide. The reaction pressure was maintained constant (±0.5 barg) by feeding gas from the ballast vessel throughout the course of the experiment. Gas uptake from the ballast vessel was measured using data logging facilities. When the gas uptake had ceased the autoclave was cooled to ambient temperature and the liquid composition was analysed by gas chromatography.

The autoclave charges for Experiment A and Example 1 are shown in Table 1. The reaction temperature and pressure for Experiment A and Example 1 are shown in Table 2 together with rate data at two calculated ethyl propionate concentrations.

The results of analysis of the liquid reaction composition at the and of the experiment by gas chromatography are shown in Table 3.

Experiment A is not an example according to the present invention because ruthenium and/or osmium promoter is not present in the liquid reaction composition.

Example 1 is an example according to the present invention because ruthenium is present in the liquid reaction composition and shows that ruthenium promotes the rate at which ethyl propionate is carbonylated to give propionic acid.

TABLE 1

Autoclave charge.

| Experiment | Ethyl propionate (g) | Propionic acid (g) | Ethyl iodide (g) | Water (g) | Promoter | Amount (g) | Catalyst | Amount[a] (g) |
|---|---|---|---|---|---|---|---|---|
| Experiment A | 16.0 | 22.1 | 6.0 | 5.7 | — | — | $H_2IrCl_6$ | 0.21 |
| Example 1 | 16.0 | 21.9 | 6.0 | 5.7 | $[\{Ru(CO)_3Cl_2\}_2]$ | 0.27 | $H_2IrCl_6$ | 0.21 |

[a]Weight expressed as grams of pure $H_2IrCl_6$. Catalyst added as 22.2% w/w aqueous Ir solution (supplied by Johnson Matthey). Catalyst dissolved in 5.0 g of the propionic acid charge and 2.5 g of the water charge.

TABLE 2

Rate data

| Experiment | Pressure (barg) | Temp. (°C.) | Promoter | Rate (mol/l/hr) at 26% w/w ethyl propionate concentration | Rate (mol/l/hr) at 16% w/w ethyl propionate concentration |
|---|---|---|---|---|---|
| Experiment A | 22 | 190 | — | 1.9 | 1.0 |
| Example 1 | 22 | 190 | $[\{Ru(CO)_3Cl_2\}_2]$ | 3.8 | 1.6 |

TABLE 3

Liquid product analysis and reaction conditions

| Experiment | Promoter | Reaction time (minutes) | Propionic acid (% w/w/) | Ethyl propionate (% w/w) | Ethyl iodide (% w/w) |
|---|---|---|---|---|---|
| Experiment A | — | 133 | 77.6 | 3.4 | 9.3 |
| Example 1 | $[\{Ru(CO)_3Cl_2\}]$ | 110 | 76.3 | 2.2 | 8.5 |

FURTHER EXPERIMENTS (EXAMPLES 2 TO 4 AND COMPARATIVE EXPERIMENT B)

Further experiments were performed using a 300 ml zirconium autoclave equipped with a Dispersimax (Trade Mark) stirrer, liquid catalyst injection facility and cooling coils. A gas supply to the autoclave was provided from a ballast vessel, feed gas being provided during the course of an experiment to maintain the autoclave at a constant pressure.

EXAMPLE 2

$[Ru_3(CO)_{12}]$ (1.66 g) and acetic acid (10.0 g) were charged to the autoclave. The autoclave was pressure tested with nitrogen and then vented via a gas sampling system. The autoclave was flushed several times with carbon monoxide. Acetic acid (20.45 g), methyl acetate (30.01 g), ethyl acetate (35.91 g), water (14.37 g), methyl iodide (10.25 g), and ethyl iodide (11.23 g) were then charged to the autoclave via a liquid addition port. The autoclave was pressurised with carbon monoxide to 8 barg and heated with stirring (1500 rpm) to 190° C. Once stable at temperature, the autoclave pressure was increased to 25 barg by feeding carbon monoxide from the ballast vessel. The catalyst, $H_2IrCl_6$ (0.641 g), dissolved in acetic acid (10.00 g)/water (5.71 g) was then injected using an overpressure of carbon monoxide to give a total reactor pressure of 28 barg. The reactor pressure was maintained at a constant value (28±0.5 barg) by feeding carbon monoxide from the ballast vessel. The reaction temperature was maintained within ±1° C. of the desired reaction temperature, 190° C., by means of a heating mantle connected to a Eurotherm (Trade Mark) control system. In addition, excess heat of reaction was removed by means of cooling coils. After 22 minutes the heater was turned off and the ballast vessel isolated. The reactor was then crash cooled by means of the cooling coils. 0.596 moles of carbon monoxide were consumed from the ballast vessel. The off-gas vented from the autoclave was analysed by GC and contained 6.2% v/v hydrogen, 4.2% v/v, carbon dioxide, 6.9% v/v methane, 2.6% v/v ethane and <0.1% v/v ethylene. Gas Chromatographic analysis showed the liquid composition recovered from the autoclave to contain 67% w/w acetic acid, 4.6% w/w propionic acid, 0.1% w/w methyl acetate, 11.1% w/w ethyl acetate, 0.1% w/w methyl iodide and 10.5% w/w ethyl iodide.

This is an example according to the current invention and demonstrates the co-production of acetic and propionic acids by carbonylation of a mixed methyl acetate/ethyl acetate and water feed using a ruthenium promoted iridium catalyst.

EXAMPLE 3

Acetic acid (37.14 g), methyl acetate (60.02 g), water (14.37 g), methyl iodide (20.50 g) and $[Ru_3(CO)_{12}]$ (1.66 g) were charged to the autoclave. The autoclave was flushed with carbon monoxide/ethylene 4:1 and pressurised with carbon monoxide/ethylene 4:1 to 8 barg. The autoclave was then heated with stirring (1500 rpm) to 190° C. Once stable at temperature the autoclave pressure was increased to 25 barg by feeding carbon monoxide/ethylene 4:1 from the ballast vessel. The catalyst, $H_2IrCl_6$ (0.642 g), dissolved in acetic acid (10.04 g)/water (5.84 g), was then injected using an overpressure of carbon monoxide to give a total reactor pressure of 28 barg. The reactor pressure was maintained at a constant value (28±0.5 barg) by feeding carbon monoxide/ethylene, 4:1, from the ballast vessel. The reaction temperature was maintained within ±1° C. of the desired reaction temperature, 190° C., by means of a heating mantle connected to a Eurotherm (Trade Mark) control system. In addition, excess heat of reaction was removed by means of cooling coils. Once gas uptake had ceased, 22 minutes, the heater was turned off and the ballast vessel isolated. The reactor was then crash cooled by means of the cooling coils.

1.173 moles of gas (carbon monoxide/ethylene at a 4:1 volumetric ratio) were consumed from the ballast vessel. The off-gas vented from the autoclave was analysed by Gas Chromatography and contained 1.2% v/v hydrogen, 2.3% v/v carbon dioxide, 8.4% v/v methane, 0.8% v/v ethane and 1.7% v/v ethylene. Gas Chromatographic analysis showed the liquid composition recovered from the autoclave to contain 77% w/w acetic acid, 9.1% w/w propionic acid, 0.4% w/w methyl acetate, 0.1% w/w ethyl acetate, 7.7% w/w methyl iodide and 0.2% w/w ethyl iodide.

This is an example according to the present invention and demonstrates the co production of acetic and propionic acids by carbonylation of a mixed methyl acetate/ethylene and water feed using a ruthenium promoted iridium catalyst.

Experiment B

The autoclave was pressure tested with nitrogen and then vented via a gas sampling system. The autoclave was then flushed several times with carbon monoxide/ethylene 4:1. Acetic acid (45.31 g), methyl acetate (60.03 g), water (14.40 g) and methyl iodide (13.97 g) were then charged to the autoclave via a liquid addition port. The autoclave was pressurised with carbon monoxide/ethylene 4:1 to 8 barg and heated with stirring (1500 rpm) to 190° C. Once stable at temperature the autoclave pressure was increased to 25 barg by feeding carbon monoxide/ethylene 4:1 from the ballast vessel. The catalyst, $H_2IrCl_6$ (0.643 g), dissolved in acetic acid (10.01 g)/water (5.71 g), was then injected using an overpressure of carbon monoxide to give a total reactor pressure of 28 barg. The reactor pressure was maintained at a constant value (28±0.5 barg) by feeding carbon monoxide/ethylene 4:1 from the ballast vessel. The reaction temperature was maintained within ±1° C. of the desired reaction temperature by means of a heating mantle connected to a Eurotherm (Trade Mark) control system. In addition, excess heat of reaction was removed by means of cooling coils. After 27 minutes the heater was turned off and the ballast vessel isolated. The reactor was then crash cooled by means of the cooling coils. 0.875 moles of gas (carbon monoxide/ethylene at a 4:1 volumetric ratio) were consumed from the ballast vessel. The off-gas vented from the autoclave was analysed by gas chromatographic and contained 2.3% v/v hydrogen, 2.6% v/v carbon dioxide, 4.2% v/v methane, 0.2% v/v ethane and 1.9% v/v ethylene. Gas chromatographic analysis showed the liquid composition recovered from the autoclave to contain 77% w/w acetic acid and 5.9% w/w propionic acid.

This is not an example according to the present invention because no ruthenium or osmium promoter was present in the liquid reaction composition.

EXAMPLE 4

Experiment B was repeated in the presence of a ruthenium promoter. $[Ru(CO)_4I_2]$ (1.46 g) and acetic acid (10.0 g) were charged to the autoclave. The autoclave was pressure tested with nitrogen and then vented via a gas sampling system. The autoclave was then flushed several times with carbon monoxide/ethylene 4:1. Acetic acid (33.87 g), methyl acetate (60.02 g), water (14.39 g) and methyl iodide (13.97 g) were then charged to the autoclave via a liquid addition port. The autoclave was pressurised with carbon monoxide/ethylene 4:1 to 8 barg and heated with stirring (1500 rpm) to 190° C. Once stable at temperature the autoclave pressure was increased to 25 barg by feeding carbon monoxide/ethylene 4:1 from the ballast vessel. The catalyst, $H_2IrCl_6$ (0.643 g), dissolved in acetic acid (10.00 g)/water (5.72 g), was then injected using an overpressure of carbon monoxide to give a total reactor pressure of 28 barg. The reactor pressure was maintained at a constant value (28±0.5 barg) by feeding carbon monoxide/ethylene 4 1 from the ballast vessel. The reaction temperature was maintained within ±1° C. of the desired reaction temperature by means of a heating mantle connected to a Eurotherm (Trade Mark) control system. In addition, excess heat of reaction was removed by means of cooling coils. Once gas uptake had ceased, 27 minutes, the heater was turned off and the ballast vessel isolated. The reactor was then crash cooled by means of the cooling coils.

1.245 moles of gas (carbon monoxide/ethylene at a 4:1 volumetric ratio) were consumed from the ballast vessel. The off-gas vented from the autoclave was analysed by gas chromatography and contained 0.2% v/v hydrogen, 2.2% v/v carbon dioxide, 4.6% v/v methane, 0.4% v/v ethane and 1.9% v/v ethylene. Gas chromatographic analysis showed the liquid composition recovered from the autoclave to contain 77% w/w acetic acid and 11.8% w/w propionic acid. This is an example according to the present invention and demonstrates the co-production of acetic and propionic acids by carbonylation of a mixed methyl acetic/ethylene and water feed using a ruthenium promoted iridium catalyst. Comparison of Example 4 with Experiment B demonstrates the beneficial effect of ruthenium on the propionic acid yield. This is illustrated in Table 4 below.

TABLE 4

| Experiment | Reaction time (minutes) | Propionic acid (% w/w[a]) |
|---|---|---|
| Comparative Experiment B | 27 | 5.9 |
| Example 4 | 27 | 11.8 |

[a] By gas chromatographic analysis of recovered liquid composition.

The rate of gas uptake at a certain point in the reaction was used to calculate the carbonylation rate, based upon moles of carbon monoxide consumed per liter of cold degassed reactor composition per hour (mol/l/hr). Carbonylation rates for Example 4, calculated at certain points in the reaction run, are compared with those calculated for Experiment B in Table 5 and demonstrate the promotional effect of ruthenium on the carbonylation rate.

TABLE 5

| Experiment | Moles of gas consumed (a) | Carbonylation rate (mol/l/hr) (b) | Moles of gas consumed (a) | Carbonylation rate (mol/l/hr$^{(b)}$) |
|---|---|---|---|---|
| Example 4 | 0.311 | 30.2 | 0.623 | 32.6 |
| Comparative Experiment B | 0.311 | 14.8 | 0.623 | 9.0 |

$^{a)}$Number of moles of combined carbon monoxide/ethylene feed consumed from the ballast vessel.
$^{b)}$Based upon moles of carbon monoxide consumed per liter of cold degassed reactor composition per hour.

I claim:

1. A process for the carbonylation of a carbonylatable reactant having a carbonylatable moiety having at least two carbon atoms and/or a reactive derivative thereof which process comprises contacting said carbonylatable reactant and/or a reactive derivative thereof with carbon monoxide in a liquid reaction composition in a carbonylation reactor characterized in that the liquid reaction composition comprises:
   (a) an iridium catalyst;
   (b) a halide;
   (c) at least a finite concentration of water;
   (d) a carbonylatable reactant selected from the group consisting of:
      a monofunctional alkyl diol, a monofunctional alkyl polyol, a cyclic ester having 3 to 6 carbon atoms, and/or a reactive derivative thereof; and,
   (e) as promoter, at least one of ruthenium and osmium.

2. A process as claimed in claim 1 in which the carbonylatable reactant is a C2 to C6 monofunctional alkyl diol.

3. A process as claimed in claim 1 in which the carbonylatable reactant is a C2 to C4 monofunctional alkyl diol.

4. A process as claimed in claim 3 in which the carbonylatable reactant is 1, 4-butanediol.

5. A process as claimed in claim 1 in which the carbonylatable reactant is a C2 to C6 monofunctional alkyl polyol.

6. A process as claimed in claim 5 in which the carbonylatable reactant is a C2 to C4 monofunctional alkyl polyol.

7. A process as claimed in claim 1 in which the carbonylatable reactant is a cyclic ester having 3 to 6 carbon atoms.

8. A process as claimed in claim 7 in which the cyclic ester is a lactone.

9. A process as claimed in claim 8 in which the lactone cyclic ester is valeractone.

10. A process as claimed in claim 1 in which the partial pressure of CO in the reactor is less than 15 bar.

11. A process for the carbonylation of a carbonylatable reactant having a carbonylatable moiety having at least two carbon atoms and/or a reactive derivative thereof which process comprises contacting said carbonylatable reactant and or a reactive derivative thereof with carbon monoxide in a liquid reaction composition of a carbonylation reactor characterized in that the liquid reaction composition comprises:
   (a) an iridium catalyst;
   (b) a halide;
   (c) at least a finite concentration of water;
   (d) a carbonylatable reactant selected from the group consisting of:
      a monofunctional olefin,
      a monofunctional diene and/or a reactive derivatives thereof; and,
   (e) as promoter, at least one of ruthenium and osmium.

12. A process as claimed in claim 11 in which the carbonylatable reactant is a C2 to C6 monofunctional olefin.

13. A process as claimed in claim 12 in which the carbonylatable reactant is a C2 to C4 monofunctional olefin.

14. A process as claimed in claim 11 in which the carbonylatable reactant is ethylene.

15. A process as claimed in claim 11 in which the carbonylatable reactant is a C4 to C6 diene.

16. A process as claimed in claim 15 in which the carbonylatable reactant is butadiene.

17. A process as claimed in claim 11 in which the partial pressure of CO in the reactor is less than 15 bar.

* * * * *